United States Patent [19]

Pelah et al.

[11] Patent Number: 5,187,308

[45] Date of Patent: Feb. 16, 1993

[54] PROCESS FOR THE PRODUCTION OF LOW VISCOSITY COPOLYMERS FROM MALEIC ACID MONOALKYL ESTERS AND VINYL ALKYL ETHERS

[75] Inventors: Zvi Pelah, Savyion, Israel; Istvan Potencsik, Mannheim, Fed. Rep. of Germany; Werner Kopp, Harthausen, Fed. Rep. of Germany; Ernst Urmann, Ludwigshafen, Fed. Rep. of Germany

[73] Assignee: Giulini Chemie GmbH, Ludwigshafen, Fed. Rep. of Germany

[21] Appl. No.: 612,389

[22] Filed: Nov. 14, 1990

[30] Foreign Application Priority Data

Nov. 15, 1989 [DE] Fed. Rep. of Germany ....... 3937982

[51] Int. Cl.$^5$ ........................................... C07C 67/465
[52] U.S. Cl. ..................................... 560/202; 424/70; 424/71; 560/190; 560/201; 560/204
[58] Field of Search ............... 560/202, 201, 190, 204; 424/70, 71

[56] References Cited

U.S. PATENT DOCUMENTS

| | | | |
|---|---|---|---|
| 2,782,182 | 2/1957 | Verburg | 526/27.1 |
| 3,530,101 | 9/1970 | Haynes et al. | 526/27.1 |
| 3,632,561 | 1/1972 | Gibb et al. | 526/27.1 |
| 4,908,413 | 3/1990 | Goertz et al. | 525/304 |
| 4,952,558 | 8/1990 | Goertz et al. | 526/27.1 |

FOREIGN PATENT DOCUMENTS

| | | |
|---|---|---|
| 3712265 | 10/1988 | Fed. Rep. of Germany . |
| 1117515 | 6/1968 | United Kingdom . |
| 1233468 | 5/1971 | United Kingdom . |

*Primary Examiner*—José G. Dees
*Assistant Examiner*—Vera C. Clarke
*Attorney, Agent, or Firm*—Spencer, Frank & Schneider

[57] ABSTRACT

The present invention relates to a novel process for the production of low viscosity copolymers of maleic acid monoalkyl ester and vinyl alkyl ethers characterized in that the copolymerization of alkyl vinyl ether is performed with a mixture composed of maleic acid anhydride and maleic acid monoalkyl ester. The specific viscosity is controlled by the setting of a certain maleic acid anhydride to maleic acid monoalkyl ester ratio.

5 Claims, 1 Drawing Sheet

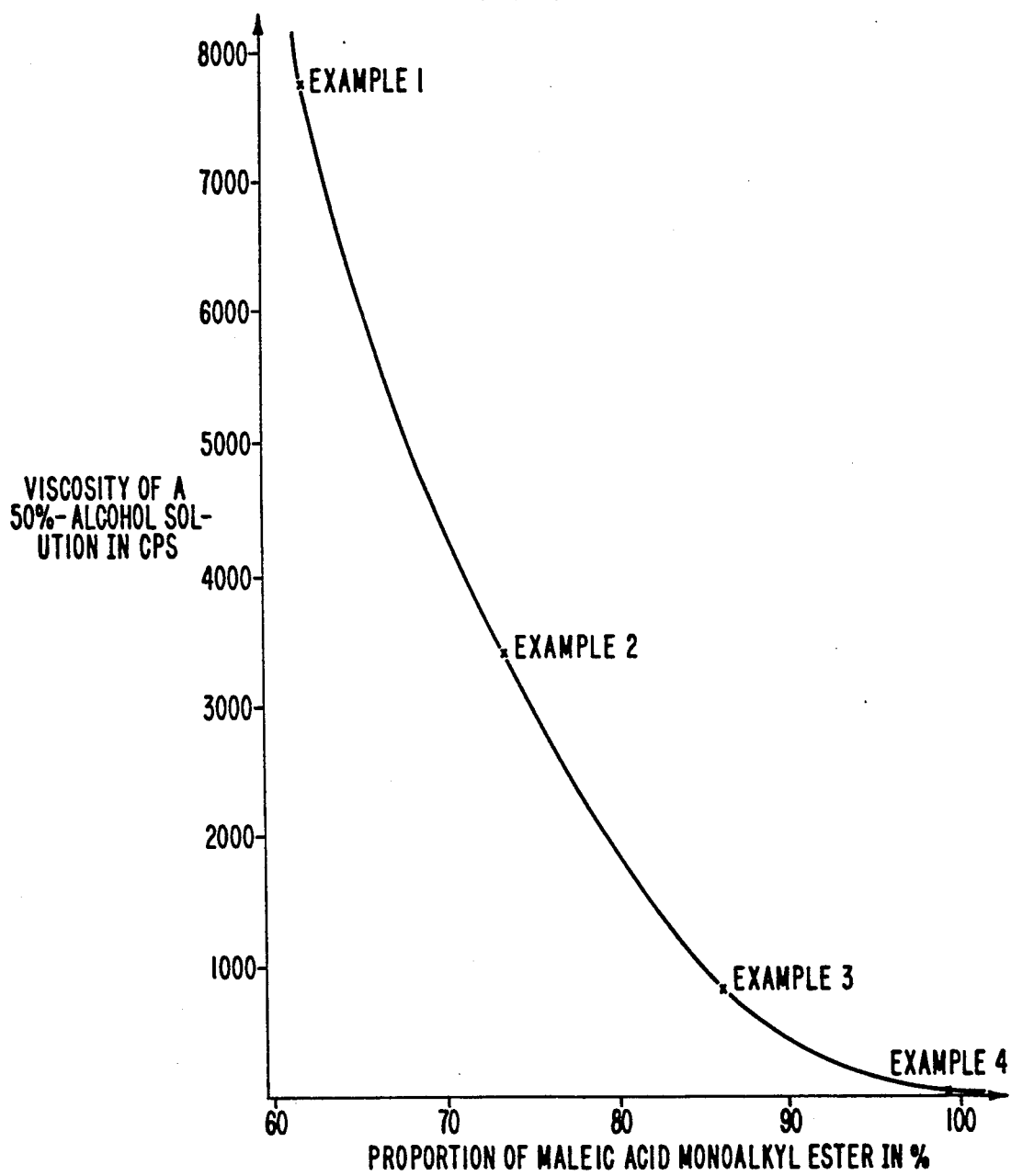

PROCESS FOR THE PRODUCTION OF LOW VISCOSITY COPOLYMERS FROM MALEIC ACID MONOALKYL ESTERS AND VINYL ALKYL ETHERS

It is the object of the present invention to provide a novel process for the production of low viscosity copolymers of maleic acid monoalkyl esters and vinyl alkyl ethers.

BACKGROUND OF THE INVENTION

Copolymers of maleic acid monoalkyl esters and vinyl alkyl ethers are known in the art. They are used in the preparation of cosmetics, primarily for hair sprays, where they are included as film-forming components. Known in this connection are the half esters including ethanol and butanol whose general formula is given below, where $R^1=CH^3$ and $R^2=$ methyl or ethyl or propyl:

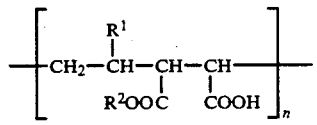

Several processes for the production of the half esters are disclosed in the literature, with all having in common that the half esters are formed by osterification of maleic anhydride/alkyl vinyl ether copolyemrs, hereinafter called MSA/AVE. Numerous processes are also known for the production of the MSA/AVE copolymers.

Some of these processes employ benzene or toluene as the solvent, for example U.S. Pat. No. 2,782,182. The production of highly molecular maleic anhydride/alkyl vinyl ethers is disclosed in British Patent No. 1,117,515. In this process, methylene chloride is employed as the solvent.

There are some more recent processes which are able to operate without solvents. For example, German Patent No. 3,712,265 discloses a process characterized in that the radical copolymerization is effected in an excess of alkyl vinyl ether, with the alkyl vinyl ether here performing the dual function of solvent and reactant. The copolymers according to this process are highly molecular and are particularly well suited for the production of dental adhesives. However, due to their high viscosity, these copolymers are not suitable as starting material for the production of half esters.

Processes for producing half esters are disclosed, for example, in DE-OS 1,930,009 and British Patent No. 1,233,468. Since, however, it was always a solvent-containing /AVE copolymer which was esterified, the resulting half esters inevitably also contain solvents. As mentioned above, the presence of even the smallest solvent residue is undesirable in cosmetic formulations and is even forbidden by law in some countries.

The production of copolymers of maleic acid monoalkyl esters and alkyl vinyl ethers is disclosed in DE-OS 3,733,158. This process is characterized in that in each polymerization phase the vinyl alkyl ether component is present in excess in the reaction mixture, the radical copolymerization takes place in acetone and the acetone is removed by distillation during or after the ester formation at temperatures up to 70° C. The products produced by this process, which are further processed as alcoholic solutions, still contain small quantities of acetone (column 5, line 23) which may lead to skin irritation in cosmetic formulations and is therefore undesirable.

It has therefore been the continued desire to obtain half esters which are absolutely free of solvents and are low in viscosity, particularly for cosmetic formulations. Attempts have also been made to find a process according to which the viscosity of the half esters could be easily controlled by varying the reaction parameters and which yields products that are also suitable for use as cosmetics. The actuality of this art is emphasized by German Patent Applications DE-OS 3,733,158 and 3,736,996 which were laid open only in 1989, with the latter relating to a process for the production of MA/AVE copolymers.

SUMMARY OF THE INVENTION

The present invention provides a process for the production of a low viscosity copolymer of malice acid monoalkyl ester and vinyl alkyl ether by radical precipitation polymerizing excess alkyl vinyl ether with a mixture comprising maleic acid anhydride and maleic acid monoalkyl ester that are in a ratio of between 1:99 and 99:1 and radical initiators, and includes setting the ratio of the maleic acid anhydride to maleic acid monoalkyl ester to control the chain length of the copolymer and its specific viscosity.

BRIEF DESCRIPTION OF THE DRAWINGS

The Figure shows the relationship between the viscosity of a 50% alcohol solution and the percentage of maleci acid monoaliyl ester. The viscosity decreases with increasing maleic acid half ester concentation.

DETAILED DESCRIPTION OF THE INVENTION

Surprisingly, the present invention was able to overcome the above-mentioned drawbacks. It is characterized in that the copolymerization of alkyl vinyl ether is effected with a mixture composed of maleic anhydride and maleic acid monoalkyl ester. The ratio of maleic anhydride to maleic acid monoalkyl ester here lies between 1 : 99 and 99 : 1. The polymerization is performed as a radical precipitation polymerization, with known radical initiators being employed and the vinyl alkyl ether component which is present in excess serving as solvent as well as commoner. The complete conversion to half ester may be effected with lower aliphatic alcohols, e.g., with methanol or ethanol or propanol or butanol.

In practice, the maleic acid monoethyl ester is initially produced separately. Then a mixture composed of the maleic acid monoethyl ester and maleic anhydride is produced and this mixture is transferred into a suitable autoclave and the radical initiator is added. The autoclave is closed, evacuated and the alkyl vinyl ether is introduced. Once the stirring device has been put into operation, the temperature is raised for two hours through the double jacket of the autoclave until all maleic anhydride is dissolved. The heating system is now adjusted in such a way that the temperature in the reaction chamber increases by 1° C. every 15 minutes. After six hours the conversion is completed. The excess alkyl vinyl ether is extracted. The end product, as a function of the maleic anhydride to maleic acid monoalkyl ether ratio, is either a powdered solid or a highly viscous, light-yellow liquid which is mixed with ethanol and reheated by reflux condensation. This yields the ethyl vinyl half ester of the maleic anhydride/methyl vinyl ether copolymer.

The control of the chain length of the copolymer and its specific viscosity are realized by setting a defined maleic anhydride/maleic acid monoalkyl ester ratio as indicated in the attached graphic illustration and the examples.

Of course all other half esters, e.g. monobutyl esters, mono-i-propyl esters, etc. can be produced by this process. The starting material is a mixture composed of maleic anhydride and the half ester of maleic anhydride and the respective alcohol, and the reaction product at the end of the copolymerization process is dissolved in the respective alcohol and is boiled together with it during the reflux condensation. In the selection of the ether component, lower alkyl vinyl ethers containing 1 to 4 carbon atoms should be given preference.

Example A below describes the production of maleic acid monoethyl ester. Examples 1 to 4 describe the production of the copolymers according to the invention, with the ratio of maleic anhydride to maleic acid monoalkyl ester being varied in each case.

EXAMPLE A

A two-liter triple necked flask equipped with reflux condenser, thermometer and KPG stirrer is filled with 1000 ml ethanol and, after the addition of 250 g maleic acid anhydride, is heated by reflux condensation until it boils.

After the maleic anhydride has been completely dissolved, this state is maintained for another 30 minutes and then the reflux condenser is exchanged for a distillation bridge. The excess ethanol is distilled off. The maleic acid monoethyl ester yield is 358 g (97.5 % of the dry substance).

EXAMPLE 2

A BüCHI autoclave equipped with a pressure resistant one-liter glass vessel, an anchor agitator and heatable double jacket is filled with 70 g of the maleic acid ethyl ester produced in Example 1 and 30 g solid, powdered maleic acid anhydride. After the addition of 100 mg dilauroyl peroxide, the autoclave is closed and evacuated. Under its own pressure or at a slight excess $N_2$ pressure, 300 ml methyl vinyl ether are filled in and the autoclave is closed. The stirrer is switched on and the temperature is raised through the double jacket within two hours from 21° C. to 40° C. until all maleic acid anhydride is dissolved. The heating system is now adjusted in such a way that the temperature in the reaction chamber increases about 1° C. every 15 minutes. After six hours, the monomer anhydride and the half ester have been completely converted.

The excess methyl vinyl ether is extracted and 148 g of a highly viscous yellow liquid remain. This liquid is mixed with 174 g ethanol and heated under reflux condensation until it boils. The result is the ethyl half ester of the MSA/MVE copolymer in a 50% ethanol solution and has a viscosity of 7800 cps (Brookfield RV, column 4; 10 rpm).

Examples 1 to 4 are compiled in Table 1. FIG. 1 shows the relationship between the viscosity of a 50% alcohol solution and the percentage of maleic acid monoalkyl ester. It can be seen directly that the viscosity decreases with increasing maleic acid half ester concentration.

TABLE 1

| Example No. | | 1 | 2 | 3 | 4 |
|---|---|---|---|---|---|
| maleic anhydride | [g] | 30 | 20 | 6 | 0.5 |
| | [mol] | 0.306 | 0.204 | 0.061 | 0.005 |
| maleic acid ethyl half ester | [g] | 70 | 80 | 54 | 70 |
| | [mol] | 0.486 | 0.555 | 0.375 | 0.486 |
| MA + MS ethyl half ester | [mol] | 0.792 | 0.759 | 0.436 | 0.491 |
| methyl vinyl ether | [ml] | 300 | 300 | 150 | 150 |
| | [g] | 225 | 225 | 112.5 | 112.5 |
| | [mol] | 3.87 | 3.87 | 1.94 | 1.94 |
| dilauroyl peroxide | [mg] | 100 | 100 | 70 | 70 |
| | [mmol] | 0.251 | 0.251 | 0.176 | 0.176 |
| ratio of MA + MSEHE: dilauroyl peroxide | | 3155:1 | 3024:1 | 2477:1 | 2790:1 |
| ratio of MA:MS ethyl half ester | [mol %] | 38.6:61.4 | 26.9:73.1 | 14.0:86.0 | 1.0:99.0 |
| reaction temperature | [°C.] | 60 | 60 | 60 | 60 |
| reaction pressure | [bar] | 3.8–4.3 | 3.8–4.3 | 3.8–4.3 | 3.8–4.3 |
| reaction time | [h] | 5 | 5 | 5 | 5 |
| viscosity of a 50% alcohol sol. | [cps] | 7800 | 3400 | 800 | 35 |

We claim:

1. A process for producing a low viscosity copolymer of maleic anhydride and a vinyl alkyl ether comprising the consecutive steps:
    a) mixing maleic anhydride with maleic acid monalkyl ester in a ratio of between 1:99 and 99:1;
    b) radical precipitation polymerizing an excess of a vinyl alkyl ether as commoner with said mixture of maleic anhydride and maleic acid monoalkyl ester as another commoner, and a radical initiator, at a temperature between 20° C. and 40° C. to produce a copolymer;
    c) removing excess vinyl alkyl ether from said copolymer; and
    d) reacting said copolymer with a lower aliphatic alcohol of formula R—OH, wherein R is an alkyl having 1 to 4 carbons, to produce an alkyl half user of the maleic anhydride/vinyl alkyl ether copolymer.

2. The process according to claim 1, wherein said vinyl alkyl ether is a lower ether of formula R—O—R', and wherein R is vinyl and R' is an alkyl selected from the group consisting of methyl, ethyl, propyl and butyl.

3. The process according to claim 1, wherein said vinyl alkyl ether is vinyl methyl ether.

4. The process according to claim 1, wherein said radical initiator is dcilauroyl peroxide.

5. The process according to claim 1, further comprising before said mixing step a step comprising preparing maleic acid monoalkyl ester by reacting maleic anhydride with an alcohol, and removing excess alcohol.

* * * * *